US006239120B1

(12) United States Patent
Hallgren et al.

(10) Patent No.: US 6,239,120 B1
(45) Date of Patent: May 29, 2001

(54) METHOD AND MEANS FOR TREATING GLOMERULONEPHRITIS

(75) Inventors: Roger Hallgren, Balinge; Bengt Fellstrom, Knivsta, both of (SE)

(73) Assignee: Pharmalink AB, Upplands Vasby (SE)

( * ) Notice: Subject to any disclaimer, the term of this patent is extended or adjusted under 35 U.S.C. 154(b) by 0 days.

(21) Appl. No.: 09/266,023

(22) Filed: Mar. 11, 1999

Related U.S. Application Data
(60) Provisional application No. 60/080,274, filed on Apr. 1, 1998.

(30) Foreign Application Priority Data

Mar. 17, 1998 (SE) .................................................... 9800905

(51) Int. Cl.⁷ .............................. C07J 71/00; A61K 31/58
(52) U.S. Cl. .............................................. 514/174; 540/63
(58) Field of Search ................................ 424/451, 464; 514/174; 540/63

(56) References Cited

U.S. PATENT DOCUMENTS

| | | | | |
|---|---|---|---|---|
| 4,840,960 | * | 6/1989 | Sterzel et al. | 514/356 |
| 5,643,602 | * | 7/1997 | Ulmius | 424/462 |
| 5,719,197 | * | 2/1998 | Kanios et al. | 514/772.6 |
| 5,916,910 | * | 6/1999 | Lai | 514/423 |

FOREIGN PATENT DOCUMENTS

| | | |
|---|---|---|
| 0468555 | 1/1992 | (EP) . |
| 0502092 | 9/1992 | (EP) . |
| 9508323 | 3/1995 | (WO) . |
| 9727843 | 8/1997 | (WO) . |

OTHER PUBLICATIONS

Alamartine et al., "Comparison of pathological lesion on repeated renal biopsies in 73 patients with primary lgA glomerulonephritis: value of quantitative scoring and approach to final prognosis", *Clinical Nephorlogy*, vol. 34, No. 2, pp. 45–51, (1990).
Lai et al., "lgA nephronpathy: common nephritis leading to end–stage renal failure", *The International Journal of Artifical Organs*, vol. 17, No. 9, pp. 457–460, (1994).
Scheinman et al., "lgA Nephropathy: To Treat or Not to Treat?", *Nephron*, vol. 75, pp. 251–258, (1997).
Shu et al. "Serum immunoglobulin E in primary lgA nephronpathy", *Clinical Nephronlogy*, vol. 44, No. 2, pp. 86–90 (1995).
Goumenos et al., "Can immunosuppressive drugs slow the progres of igA nephorpathy?", *Nephrol Dial Transplant* vol. 10, pp. 1173–1181, (1995).
Schmidt et al., "The role of angiotensin I–converting enzyme gene polymorphism in renal disease" *Nephrology and Hypertension*, vol. 5, pp. 552–555, (1996).
Donadio et al., "A Controlled Trial of Fish Oil in lgA Nephorpathy", vol. 331, No. 18, pp. 1194–1199, (1994).
Trachtman et al., "Vitamin E Ameliorates Renal Injury in an Experimental Model of Immunogolbulin A Nephropathy", vol. 40, No. 4, pp. 620–626, (1996).
Feehally et al., "Immunoglobulin A nephronpathy: fish oils and beyond", *Nephrology and Hypertension*, vol. 5, pp. 442–446, (1996).
Donadio et al., "The fate of renal transplants in patients with IgA nephropathy", *Clin. Transplanation* vol. 11, pp. 127–133, (1997).
Odum et al., "Recurrent mesangial IgA nephritis following renal transplanation", *Nephrol Dial Transplant* vol. 9, pp. 309–312, (1994).
Andersson et al., "Effectr of structrual alterations on the biotransformation rate of glucocorticosteroids in rat and human liver", *Xenobiotica*, vol. 17, No. 1, pp. 35–44, (1987).
von Asmuth et al., "IL–6, IL–8 and TNF production by cytokine and popplysaccharide–stimulated human renal cortical epithelial cells in vitro", *Chemical Abstracts*, vol. 121, p. 970, (1994).
Minami et al., "Preliminary results of short–term combination immunosuppressions of mizoribine, arathiopine, and prednisolone with pretreatment to canine kidney transplantion", *J. Vet. Med.*, vol. 55, No. 3, pp. 409–414.

* cited by examiner

*Primary Examiner*—José G. Dees
*Assistant Examiner*—Konata M. George
(74) *Attorney, Agent, or Firm*—Browdy and Neimark

(57) ABSTRACT

The invention provides the use of a glucocorticoid having a first pass metabolism in the liver of at least 90% as active substance, for the manufacturing of a medicament for oral or rectal administration in the treatment of glomerulonephritis by releasing the active substance in the intestine. The invention also provides a method for treatment of glomerulonephritis in a native kidney or a kidney transplant with the glucocorticoid as defined above. The invention also comprises a composition comprising the active substance and a pharmaceutically acceptable carrier, adjuvant or diluent designed for oral or rectal administration.

14 Claims, No Drawings

METHOD AND MEANS FOR TREATING GLOMERULONEPHRITIS

CROSS REFERENCE TO RELATED APPLICATION

This application claims the benefit of U.S. provisional application No. 60/080,274 filed Apr. 1, 1998.

FIELD OF INVENTION

The present invention relates to a method and means for treating glomerulonephritis.

BACKGROUND OF THE INVENTION

The functional units of the kidney, such as the glomeruli may suffer from inflammation. An inflammatory attack in the glomeruli is termed glomerulonephritis and can be classified into subgroups such as membraneous glomerulonephritis, focal segmental glomerulosclerosis, mesangial diffuse proliferative glomerulonephritis, endocapillary or extracapillary proliferative glomerulonephritis. Using histopathological techniques these subgroups vary with respect to microscopical or immunohistochemical picture. One cause of inflammation is due to the deposition of immunoglobulin A (IgA) in glomeruli. This condition is termed IgA nephropathy (1–3), and is the most common form of glomerulonephritis in a global perspective.

Assessment of the degree of severity of glomerulonephritis is based on different investigation results. The most important findings are 1) the degree of urinary excretion of protein (proteinuria) and 2) the filtering function of the kidney, which can be assessed by serum creatinine (screatinine). Histological examination of material from kidney (renal biopsy) yields information about the type of renal damage as well as the severity of the injury. The outcome of a glomerulonephritis is variable and is dependent upon the histological and the immunohistochemical findings in a renal biopsy. Patients with IgA nephropathy having a constant proteinuria often develop renal failure and uraemia after 5 to 20 years of illness (4).

Various treatments for glomerulonephritis are known. For example substances which act on the immune system, e.g. Cyclophosphamide, Azathioprine and Cyclosporine have been used. Glucocorticoids have also been used (mainly prednisone or prednisone acetate) which may be administered orally or by venous infusion (5, 6). Unfortunately, these treatments cause severe side effects and are not particularly effective. Other suggested treatments include ACE-inhibitors (7), polyunsaturated fatty acid-preparations (8) and vitamin E (9). The treatment results for these therapies for IgA nephropathy have been quite disappointing and it has been concluded that an effective treatment against progressive IgA nephropathy is basically missing (10). For this reason, a substantial number of patients with IgA nephropathy, 20–30%, will eventually develop renal insufficiency and uraemia (1–4). The available treatment for uraemia today is dialysis or kidney transplantation. Renal transplant patients who have been transplanted because of uraemia due to glomerulonephritis frequently suffer from recurrence of glomerulonephritis in the transplant and subsequently a gradual loss of transplant function (11, 12). This is most common with patients who previously suffered from IgA nephropathy. Today there is no effective treatment against recurrence of glomerulonephritis in a transplant.

The glucocorticoids that have been used in IgA nephropathy and in other types of glomerulonephritis are characterised by a substantial gastrointestinal absorption after oral administration, aiming to exert a direct effect on circulating leukocytes and cells that have infiltrated the kidney or the renal transplant, thus having a systemic effect. Such a systemic effect is also achieved if glucocorticoids are administered as an intravenous infusion. Systemic administration of glucocorticoids may have influenced the outcome of IgA nephropathy in some cases.

BRIEF DESCRIPTION OF THE INVENTION

Surprisingly, it has now been found that glucocorticoid having a first pass metabolism in the liver of at least 90%, which minimises the systemic effect, is effective in controlling glomerulonephritis and especially IgA nephropathy in a native kidney or a kidney transplant. The substance preferably exerts its effect in the intestinal wall of a certain part of the gut (the lower third of the small intestine and the upper fourth of the large intestine). A man skilled in the art would not have expected that treatment of an apparently healthy intestine should have an effect on an inflamed kidney. This discovery represents a breakthrough in the treatment of glomerulonephritis since it has the advantage of reducing the severe side effects on the body, such as effects on skeleton, metabolism and muscles, caused by therapy with the systemic glucocorticiods used in prior art therapy.

SUMMARY OF THE INVENTION

The invention relates to the use of a glucocorticoid having a first pass metabolism in the liver of at least 90%, which gives a minimal systemic effect, for the manufacturing of a medicament for oral or rectal administration for the treatment of glomerulonephritis. More specifically the invention relates to the use of the glucocorticoid defined above for the manufacturing of a medicament for the treatment of glomeluronephritis, especially IgA nephropathy, in a native kidney or kidney transplant. The medicament is provided in a form by which the active substance is released in a pharmacologically effective amount, in the apparently healthy intestine when it passes the lower third of the small intestine and the upper fourth of the large intestine. The invention also relates to a method for the treatment of glomeluronephritis, by oral and rectal administration of a pharmacologically effective amount of a glucocorticoid preparation having a first pass metabolism in the liver of at least 90%, minimising the systemic effect. In the method according to the invention the preparation is released in the intestine when passing the lower third of the small intestine and the upper fourth of the large intestine. The invention relates more specifically to the treatment of IgA nephropathy by administering 0.1 mg to 40 mg of the active substance daily to a subject in need thereof.

According to the invention there is further provided a pharmaceutical composition comprising the glucocorticoid, in association with a pharmaceutically acceptable diluent, adjuvant or carrier, which composition is for use in the treatment of glomerulonephritis. For oral use the composition is preferably administered in a form selected from tablets, pills, capsules, syrups, suspensions, powders and granules. The solid forms of the preparation comprise a carrier and an enteric coating, and are most preferably in t he form of a capsule comprising microcapsules. When used rectally the active substance is preferably administered in a form selected from foams, suppositories, and enemas.

DETAILED DESCRIPTION OF THE INVENTION

The medicament and method according to the invention is preferably used to treat a patient who suffers from acute or chronic glomerulonephritis. Glomerulonephritis may be divided into subtypes such as membranous glomerulonephritis, focal segmental proliferative glomerulonephritis, diffuse mesangioproliferative glomerulonephritis, endocapillary or extracapillary proliferative glomerulonephritis, depending on where the inflammation is located. The medicament and method according to this invention is preferably used to treat the IgA nephropathy type of glomerulonephritis. The invention is particularly suitable for treating patients who suffered from glomerulonephritis (particularly IgA nephropathy), had a transplant, and suffered from a recurrence of glomerulonephritis (particularly IgA nephropathy) in the transplanted kidney.

The glucocorticoid used in the present invention is preferably one which has a first pass metabolism in the liver of at least 90% minimising the systemic effects. The first pass metabolism in the liver of a glucocorticoid substance can be determined using the method disclosed previously (13). More preferably it is budesonide, rofleponide or derivatives thereof, beclomethasone dipropionate, beclomethasone monopropionate, ciclesonide, tipredane, flunisolide, traimcinolone acetonide or flutiscasone propionate. Budesonide, which is a 16,17-butylidenedioxy- $11\beta,21$-dihydroxypregna-1,4-diene-3,20-dione, is particularly preferred.

The glucocorticoid, when administered orally, is generally administered in the form of tablets, pills, capsules, powders or granules, especially in the form of capsules comprising microcapsules. Also liquid preparations such as syrups and suspensions are conceivable. When administered rectally, it is in the form of foams, suppositories or enemas.

The glucocorticoid may be administered as such or as a pharmaceutical composition in combination with a pharmaceutically acceptable diluent, adjuvant or carrier. Particularly preferred are compositions not containing material capable of causing an adverse, e.g. an allergic reaction.

The glucocorticoid substance may be admixed with an adjuvant or a carrier, e.g. lactose, saccharose, sorbitol, mannitol; starches such as potato starch, corn starch or amylopectin; cellulose derivatives; a binder such as gelatin or polyvinlypyrrolidone; and a lubricant such as magnesium stearate, calcium stearate, polyethylene glycol, waxes and/or paraffin, and then compressed into tablets. If coated tablets are required, the cores, prepared as described above, may be coated with a concentrated sugar solution, which may contain e.g. gum arabic, gelatin, talcum and/or titanium dioxide. Alternatively, the tablet may be coated with a suitable polymer dissolved in a readily volatile organic solvent. The tablet preferably has an enteric coating to allow release of the glucocorticoid substance in the lower intestine. Suitable capsules may be prepared by using the methods described in EP-A-502092, WO 97/27843 or WO 95/08323.

For the preparation of soft gelatin capsules, the glucocorticoid substance may be admixed with e.g. a vegetable oil or polyethylene glycol. Hard gelatin capsules may contain granules of the substance using either the above mentioned excipients for tablets, e.g. lactose, saccharose, sorbitol, mannitol, starches, cellulose derivatives or gelatin. Also liquid or semisolid formulations of the glucocorticoid substance may be filled into hard gelatin capsules.

Liquid preparations of oral application may be in the form of syrups or suspensions, for example solutions containing the glucocorticoid substance, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in the art.

Rectal enema formulations can be in the form of simple suspensions of the glucocorticoid substance in a pharmaceutically acceptable carrier or may be in the form of a rectal foam formulation, for example as described in EP-A-468555.

The glucocorticoid substance is preferably administered at a dosage regime from 0.1 to 40 mg, more preferably from 0.5 to 20 mg, most preferably from 1 to 10 mg, either as a single dose or in divided doses from 2 to 4 times per day. The pharmaceutical composition for oral administration used in the present invention should preferably be prepared in such a way that the glucocorticoid substance is released during the passage of the lower third of the small intestine and the upper fourth of the large intestine. This is in order to achieve a high local concentration of glucocorticoid in these parts of the intestine so that the glucocorticoid exerts its effect, preferably through the intestinal wall of these parts of the intestine.

The invention is illustrated by the following examples where budesonide was administered orally using the Entocort™ preparation (tablet form) to patients suffering from IgA nephropathy in native kidneys or kidney transplants.

EXAMPLE 1

A 52-year old man fell ill with signs of renal disorder as indicated by proteinuria and red blood cells in the urine in 1982. After renal biopsy and histological analysis of renal tissue he was diagnosed with IgA nephropathy. He was treated with various antihypertensive drugs but the proteinuria increased and by 1990 he had developed renal insufficiency and later that year he developed uraemia which in turn necessitated dialysis treatment. In 1993 he received a kidney from a deceased person. The transplanted kidney was working satisfactorily for the first 24 months and the patient was treated with glucocorticoid substance with systemic effect (prednisolone) as well as with an immunosuppressive drug (Cyclosporine). In 1995 the first signs of renal disorder of the transplanted kidney were detected with increased proteinuria and reduced renal function as measured by changes in serum-creatinine concentrations. After renal biopsy of the transplant followed by histological analysis it was shown that the tissue was affected by IgA nephropathy. At this stage, treatment with budesonide (Entocort™, 9 mg/day) was initiated. Before the treatment commenced he had a considerable proteinuria (3.1 g albumin/day; normal range 0.3 g/day) and a reduced renal filtering capacity (serum creatinine 264 $\mu$mol/1; normal range 80–115 $\mu$mol/1). After treatment with budesonide both the proteinuria and the renal function improved significantly as shown in Table 1.

TABLE 1

| Time (weeks) | U-albumin (mg/24 h) | S-creatinine ($\mu$mol/l) |
| --- | --- | --- |
| 0 | 3089 | 264 |
| 6 | 624 | 213 |
| 12 | 347 | 203 |

EXAMPLE 2

A 29-year old patient (female) with IgA nephropathy, where histological examination of material from a renal biopsy disclosed irregular widening of the mesangium and a slight increase of mesangial matrix, but no cellular proliferation. She had earlier been treated with immunosuppressive and antihypertensive drugs without any success as regards improvement of renal function or decrease of proteinuria. Treatment with budesonide (9 mg/day) was initiated and after three months of treatment a 50% reduction of proteinuria was detected as disclosed in Table 2.

TABLE 2

| Time (weeks) | U-albumin (mg/24 h) | S-creatinine ($\mu$mol/l) |
|---|---|---|
| 0 | 899 | 85 |
| 6 | 745 | 75 |
| 12 | 421 | 75 |

EXAMPLE 3

A 47-year old patient (male) suffered from IgA nephropathy, which was diagnosed in August 1996. Histological examination of material from renal biopsy showed a slight to moderate widening of the mesangium, slight increase of mesangial matrix and a slight mesangial proliferation. Furthermore, focal chronic inflammation was present in the interstitium and there was focal fibrosis and partial atrophic tubuli present. Treatment with budesonide (9 mg/day) was initiated and after 12 weeks of treatment the proteinuria was reduced and the renal function (serum creatinine was improved as shown in Table 3.

TABLE 3

| Time (weeks) | U-albumin (mg/24 h) | S-creatinine ($\mu$mol/l) |
|---|---|---|
| 0 | 1349 | 147 |
| 6 | 1050 | 142 |
| 12 | 1067 | 129 |

EXAMPLE 4

A patient, 37-years old, (male) with IgA nephropathy, where histological examination of the renal biopsy demonstrated that 2/15 glomeruli were sclerotic and the other glomeruli had mesangial proliferative changes. A slight focal interstitial fibrosis and tubular atrophy could also be demonstrated. Treatment with budesonide (9 mg/day) was initiated and after 12 weeks of treatment the proteinuria was reduced and renal function was basically unchanged as shown in Table 4.

TABLE 4

| Time (weeks) | U-albumin (mg/24 h) | S-creatinine ($\mu$mol/l) |
|---|---|---|
| 0 | 1244 | 116 |
| 6 | 964 | 113 |
| 12 | 1078 | 112 |

EXAMPLE 5

A 52-year old patient (female) with IgA nephropathy, where the histological examination of material from renal biopsy showed substantial segmental sclerotic changes in 2–4/15 glomeruli and slight mesangial proliferative changes in the rest of the glomeruli. There was also slight interstitial fibrosis and tubular atrophy present. Treatment with budesonide (9 mg/day) was initiated and after 12 weeks of treatment the proteinuria was reduced and the renal function was possibly improved as shown in Table 5.

TABLE 5

| Time (weeks) | U-albumin (mg/24 h) | S-creatinine ($\mu$mol/l) |
|---|---|---|
| 0 | 634 | 106 |
| 6 | 516 | 107 |
| 12 | 431 | 100 |

EXAMPLE 6

A 26-year old patient (male) with IgA nephropathy was studied before and during the treatment with budesonide (9 mg/day). After 12 weeks roteinuria was reduced as shown in Table 6.

TABLE 6

| Time (weeks) | U-albumin (mg/24 h) | S-creatinine ($\mu$mol/l) |
|---|---|---|
| 0 | 1449 | 91 |
| 6 | 1398 | 97 |
| 12 | 1100 | 90 |

EXAMPLE 7

A 27-year old patient (female) with IgA nephropathy, where histological examination of material from the renal biopsy showed an irregular widening of the mesangium and a focal increase of mesangial matrix and a slight mesangial proliferation. The interstitium, tubuli, and vessels had normal appearances. Treatment with budesonide (9 mg/day) was initiated and after 12 weeks of treatment the proteinuria was reduced as shown in Table 7.

TABLE 7

| Time (weeks) | U-albumin (mg/24 h) | S-creatinine ($\mu$mol/l) |
|---|---|---|
| 0 | 311 | 82 |
| 6 | 212 | 81 |
| 12 | 167 | 81 |

EXAMPLE 8

A 36-year old patient (male) with IgA nephropathy, where histological examination of material from renal biopsy showed that 14/28 glomeruli were entirely sclerotic and in the rest of glomeruli there was a widening of the mesangium and a slight mesangial proliferation and an increase of mesangial matrix. Focal fibrosis was also found in the interstitium. Treatment with budesonide (9 mg/day) was initiated and after 6 weeks of treatment the proteinuria was reduced and renal function was improved as shown in Table 8.

TABLE 8

| Time (weeks) | U-albumin (mg/24 h) | S-creatinine ($\mu$mol/l) |
|---|---|---|
| 0 | 829 | 171 |
| 6 | 596 | 152 |

References

1. Clarkson et al. In Diseases of the Kidney, Braun & Co, 1988, pp 2061–2090.
2. Alarmaatine et al. Clin Nephrol 34 (2): 45, 1990.
3. Lai et al. Int J Artif Organs 17 (9): 457, 1994.
4. Scheinman et al. Nephron 75: 251, 1997.
5. Shu et al. Clin Nephrol 44: 86, 1995.
6. Goomanos et al. NDT 10: 1173, 1995.
7. Schmidt et al. Curr Op Nephrol Hypertension 5: 552, 1996.
8. Donadio et al. NEJM 3: 1194, 1994.
9. Trachtman et al. Ped Res 40: 620, 1996.
10. Feehally et al. Curr Op Nephrol Hypertension 5: 442, 1996.
11. Frohnert et al. Clin Transpl 11: 127, 1997.
12. Odum et al. NDT 9: 309, 1994.
13. Andersson P et al. Xenobiotica 17: 5, 1987.

What is claimed is:

1. A method of treating acute or chronic glomerulonephritis in a patient in need thereof comprising administering to said patient a pharmacologically effective amount of a glucocorticoid having a first pass metabolism in the liver of at least 90% in contact with the intestinal wall area.

2. The method according to claim 1 wherein the glucocorticoid exerts its effect when passing the lower third of the small intestine and the upper fourth of the large intestine.

3. The method according to claim 1, wherein the glucocorticoid is selected from budesonide, rofleponide, beclomethasone mono-propionate, beclomethasone di-propionate, ciclesonide, tipredane, flunisolide, traimcinolone acetonide and fluticasone propionate.

4. The method according to claim 3, wherein the glucocorticoid is budesonide.

5. The method according to claim 1, wherein said glucocorticoid is administered in a daily dosage of 0.1 mg to 40 mg, as a single dose or in divided doses 2 to 4 times per day.

6. The method according to claim 1, wherein the glucocorticoid is administered orally.

7. The method according to claim 6, wherein the glucocorticoid is administered in a form selected from the group consisting of tablets, pills, capsules, powders, syrups, solutions and granules.

8. The method according to claim 7, wherein said administration from comprises a carrier and an enteric coating and is preferably in the form of capsules comprising microcapsules.

9. The method of claim 1, wherein the glucocorticoid is administered rectally in a form selected from the group consisting of suppositories, foams, and enemas.

10. The method according to claim 1 for treating IgA nephropathy in a native kidney or a kidney transplant.

11. The method according to claim 3, wherein said glucocorticoid is administered in a daily dose of 0.1 mg to 40 mg as a single dose or in divided doses 2 to 4 times per day.

12. The method according to claim 4, wherein said glucocorticoid is administered in a daily dose of 0.1 mg to 40 mg as a single dose or in divided doses 2 to 4 times per day.

13. The method according to claim 1, wherein said glucocorticoid is administered in a daily dose of 0.5 mg to 20 mg as a single dose or in divided doses 2 to 4 times per day.

14. The method according to claim 1, wherein said glucocorticoid is administered in a daily dose of 1 mg to 10 mg as a single dose or in divided doses 2 to 4 times per day.

* * * * *